(12) United States Patent
Sauer (10) Patent No.: US 11,039,828 B2
(45) Date of Patent: Jun. 22, 2021

(54) PROSTHETIC SUTURING DEVICE AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 16/259,854

(22) Filed: Jan. 28, 2019

(65) Prior Publication Data

US 2019/0231344 A1 Aug. 1, 2019

Related U.S. Application Data

(60) Provisional application No. 62/622,868, filed on Jan. 27, 2018.

(51) Int. Cl.
| | | |
|---|---|---|
| *A61B 17/04* | (2006.01) | |
| *A61F 2/24* | (2006.01) | |
| *A61B 17/06* | (2006.01) | |
| *A61B 17/00* | (2006.01) | |

(52) U.S. Cl.
CPC ...... *A61B 17/0469* (2013.01); *A61B 17/0482* (2013.01); *A61B 17/06061* (2013.01); *A61B 2017/00243* (2013.01); *A61B 2017/00398* (2013.01); *A61B 2017/00783* (2013.01); *A61B 2017/0472* (2013.01); *A61F 2/24* (2013.01); *A61F 2/2409* (2013.01)

(58) Field of Classification Search
CPC ............ A61B 17/0469; A61B 17/0482; A61B 17/06061; A61B 2017/00243; A61B 2017/00783; A61B 2017/00398; A61B 2017/0472; A61F 2/2409; A61F 2/24; A61F 2/2427; A61F 2/2418; A61F 2/2466
See application file for complete search history.

(56) References Cited

U.S. PATENT DOCUMENTS

| | | | | |
|---|---|---|---|---|
| 4,185,636 A | * | 1/1980 | Gabbay | A61B 17/06061 606/148 |
| 6,464,707 B1 | * | 10/2002 | Bjerken | A61B 17/0469 606/139 |
| 6,730,102 B1 | * | 5/2004 | Burdulis, Jr. | A61B 17/0469 606/144 |
| 7,445,626 B2 | * | 11/2008 | Songer | A61B 17/0057 606/224 |
| 10,492,779 B2 | * | 12/2019 | Dang | A61B 17/0625 |

(Continued)

*Primary Examiner* — Katrina M Stransky
*Assistant Examiner* — Raihan R Khandker
(74) *Attorney, Agent, or Firm* — Christopher B. Miller; David J. Gervasi (57) ABSTRACT

A prosthetic suturing device is disclosed. The prosthetic suturing device has a housing and a needle press slideably engaged with the housing. The prosthetic suturing device also has a plurality of needles coupled to the needle press. The prosthetic suturing device further has a prosthetic retainer. The prosthetic suturing device also has a ferrule platen having a plurality of ferrule holders, each corresponding to one of the plurality of needles. The prosthetic suturing device further has an actuator configured to move the needle press from a retracted position where needle tips of the plurality of needles are away from the ferrule platen to an engaged position where the needle tips of the plurality of needles are at least partially within the ferrule holders of the ferrule platen.

23 Claims, 10 Drawing Sheets

(56) References Cited

U.S. PATENT DOCUMENTS

2002/0198543 A1* 12/2002 Burdulis ................ A61B 17/11
                                                            606/144
2009/0005794 A1*  1/2009 Lowry ............... A61B 17/0206
                                                            606/148

* cited by examiner

PROSTHETIC SUTURING DEVICE AND METHODS THEREOF

RELATED APPLICATION

This application claims priority to U.S. Provisional Patent Application No. 62/622,868 filed Jan. 27, 2018 and entitled, "PROSTHETIC SUTURING DEVICE AND METHODS THEREOF". The 62/622,868 application is hereby incorporated by reference in its entirety.

FIELD

The claimed invention relates to surgical suturing devices, and more specifically to surgical suturing devices suitable for use with prosthetic devices, especially cardiac prosthetic devices such as replacement heart valves.

SUMMARY

A prosthetic suturing device is disclosed. The prosthetic suturing device has a housing and a needle press slideably engaged with the housing. The prosthetic suturing device also has a plurality of needles coupled to the needle press. The prosthetic suturing device further has a prosthetic retainer. The prosthetic suturing device also has a ferrule platen having a plurality of ferrule holders, each corresponding to one of the plurality of needles. The prosthetic suturing device further has an actuator configured to move the needle press from a retracted position where needle tips of the plurality of needles are away from the ferrule platen to an engaged position where the needle tips of the plurality of needles are at least partially within the ferrule holders of the ferrule platen.

A method of prosthetic suturing is also disclosed. A prosthesis is retained in a prosthetic receiver of a prosthetic suturing device. A plurality of ferrules, each ferrule coupled to a different suture end, are loaded into a ferrule platen. The loaded ferrule platen is locked into the prosthetic suturing device. A plurality of needles is actuated substantially simultaneously through the retained prosthesis and into coupling contact with the plurality of ferrules loaded into the ferrule platen. The plurality of needles is retracted substantially simultaneously back through the retained prosthesis to pull the different suture ends through the prosthesis.

BACKGROUND

Modern advances in cardiac surgery have made it possible to replace heart valves using minimally invasive surgical techniques. As minimally invasive techniques have improved, surgeons are able to operate on patients through smaller and smaller access holes, resulting in less perioperative pain and shorter recovery times. A main focus of innovations in minimally invasive cardiac surgery has been on the tools which pass into the patient, through the small access holes, to place suture stitches more efficiently and reliably in tissue. By focusing on improvements to these steps of the surgical procedures, patients are able to be on cardio-pulmonary bypass (CPB) machines for shorter times, thereby improving patient outcomes. Resultant efficiency improvements while working within the patient further help to reduce stress and fatigue on surgeons.

It would also be advantageous to focus on efficiency outside of the patient. Surgical teams are regularly working to streamline their own processes to enable surgeons to be as efficient as possible. In many minimally invasive surgical procedures, the ends of sutures which have been stitched within a patient are brought back out of the patient through one of the access sites so that the suture ends can be kept organized and then stitched through a sewing ring or cuff of a prosthetic device. Unfortunately, the suture ends often have connectors which were previously used to enable a corresponding minimally invasive suturing device to manipulate the suture ends within the patient. While it might be possible to reset these connectors (and therefore the suture ends) into the minimally invasive tissue suturing device, such devices are often not compatible with suturing a sewing cuff of a prosthetic device. As a result, surgical teams may be forced to cut off the connectors and thread each suture onto a needle in order to manually stitch each suture end through a prosthetic valve's sewing cuff. Unfortunately, for many cardiac surgical procedures, this can increase the overall time a patient is on CPB. Longer CPB times are associated with complications of the inflammatory system, heart, lungs, kidneys, and brain.

It would be desirable to have a prosthetic suturing device which is compatible with automated tissue suturing devices while also facilitating suture management and reducing the amount of time ultimately needed to place a large number of sutures through a prosthetic device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1:
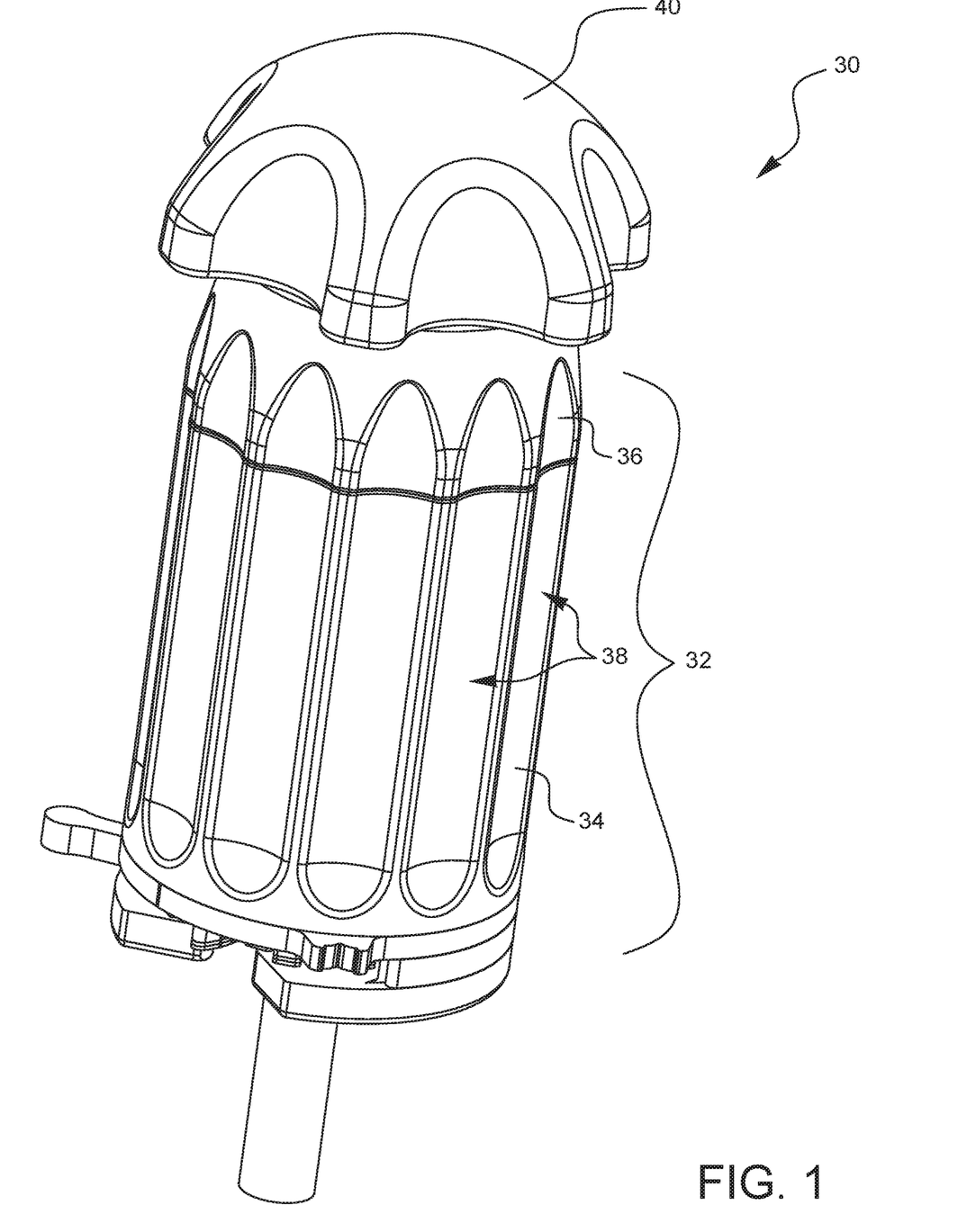
FIG. 1 is a top perspective view of one embodiment of a prosthetic suturing device.

FIG. 1 is a top perspective view of one embodiment of a prosthetic suturing device 30. The prosthetic suturing device 30 has a housing 32 which includes a main housing 34 and a top housing 36. Depending on the embodiment, the housing 30 may also include one or more grip features 38 to facilitate holding the device 30. The prosthetic suturing device 30 also has an actuator 40, the features of which will be discussed later in this specification.

Figure 2:
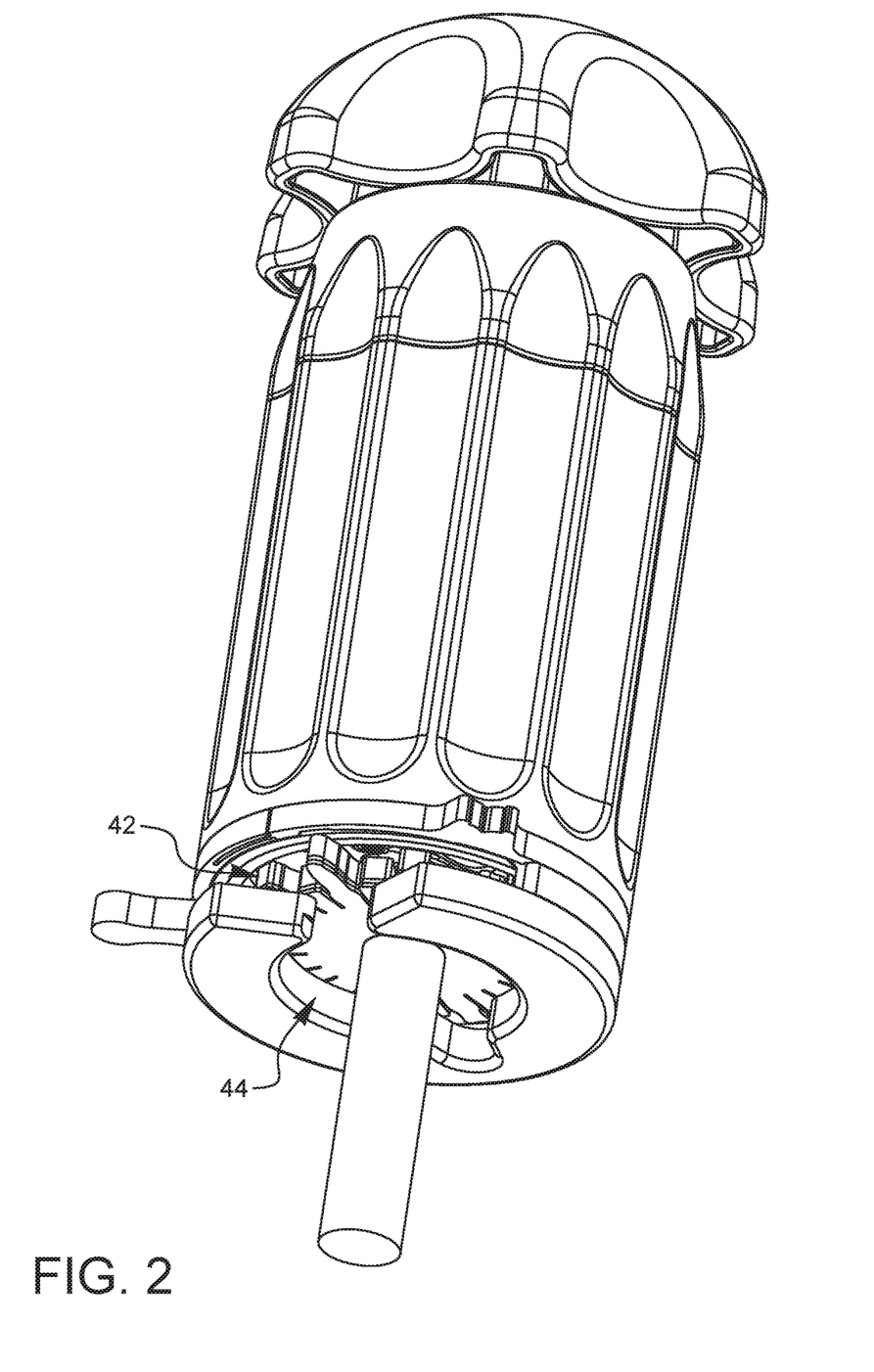
FIG. 2 is a bottom perspective view of the prosthetic suturing device of FIG. 1

FIG. 2 is a bottom perspective view of the prosthetic suturing device 30. The housing 32 defines a platen opening 42 and a prosthetic opening 44.

Figure 3:
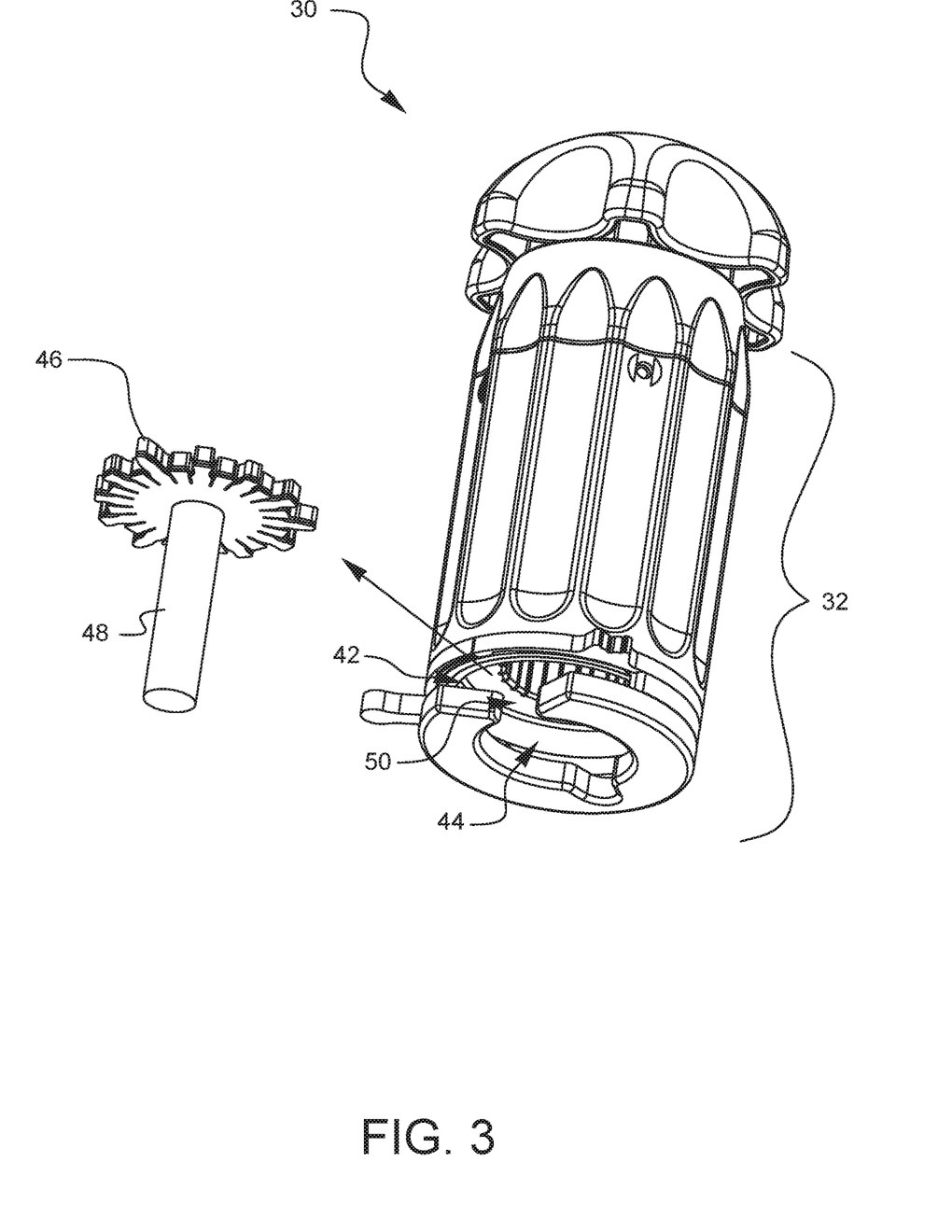
FIG. 3 is a perspective view illustrating one embodiment of a ferrule platen being removed from the prosthetic suturing device of FIG. 1.

FIG. 3 is a perspective view illustrating one embodiment of a ferrule platen 46 being removed from the prosthetic suturing device 30 via the platen opening 42. The ferrule platen 46 is coupled to a platen stem 48 which may advantageously be used to hold and manipulate the ferrule platen 46. The platen opening 42 and the prosthetic opening 44 are joined together by a stem notch 50 which is also defined by the housing 32. The stem notch 50 enables the platen stem 48 to clear the housing 32 while the platen stem 48 is being used to remove the ferrule platen 46 from the platen opening 42.

Figure 4:
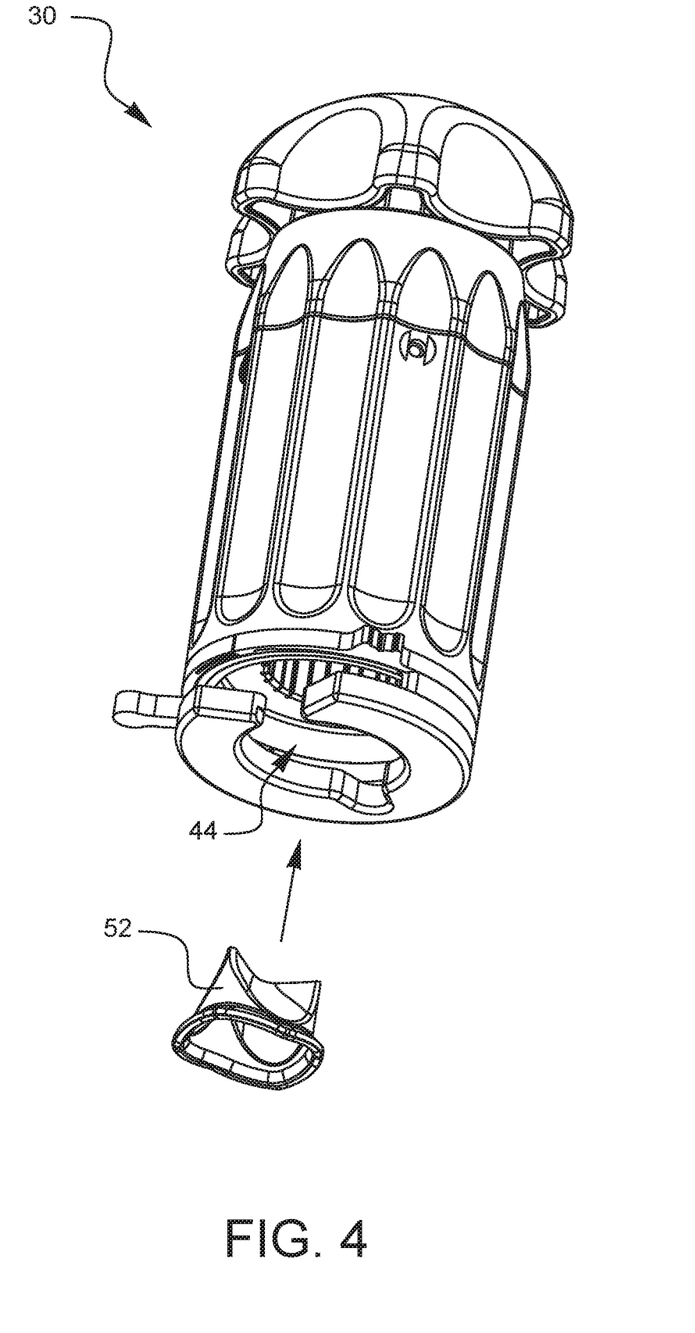
FIG. 4 is a perspective view illustrating one embodiment of a prosthetic heart valve ready to be inserted into the prosthetic suturing device of FIG. 3.
Figure 5:
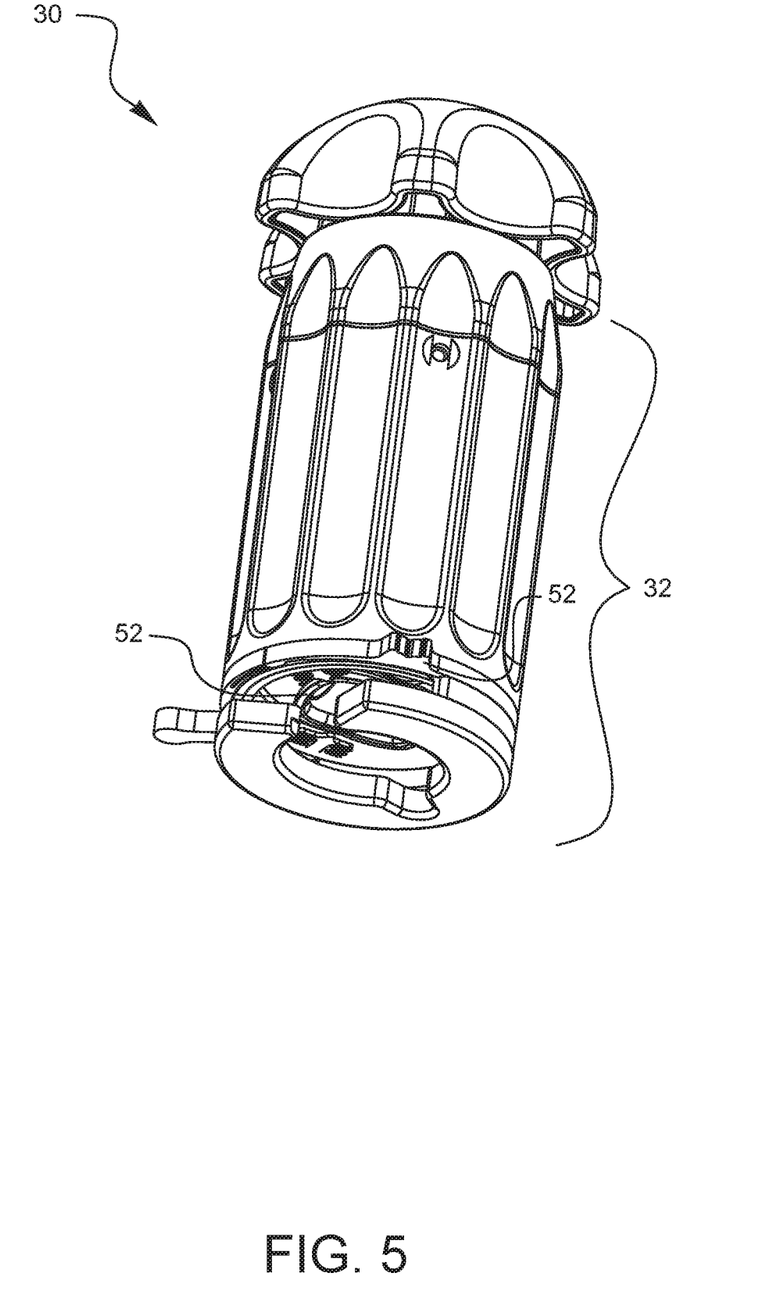
FIG. 5 is a perspective view illustrating the prosthetic heart valve of FIG. 4 inserted into the prosthetic suturing device of FIG. 3.

As illustrated in FIG. 4, when the ferrule platen 46 is removed from the prosthetic suturing device 30, a prosthetic device such as, but not limited to prosthetic heart valve 52 may be ready to be inserted into the prosthetic suturing device 30 via the prosthetic opening 44. FIG. 5 illustrates the prosthetic heart valve 52 inserted into the prosthetic suturing device 30. The device 30 has a prosthetic retainer which can be engaged to hold the prosthetic valve 52 in place. In FIG. 5, a prosthetic retainer tab 54 is visible protruding from the housing 32.

Figure 6A:
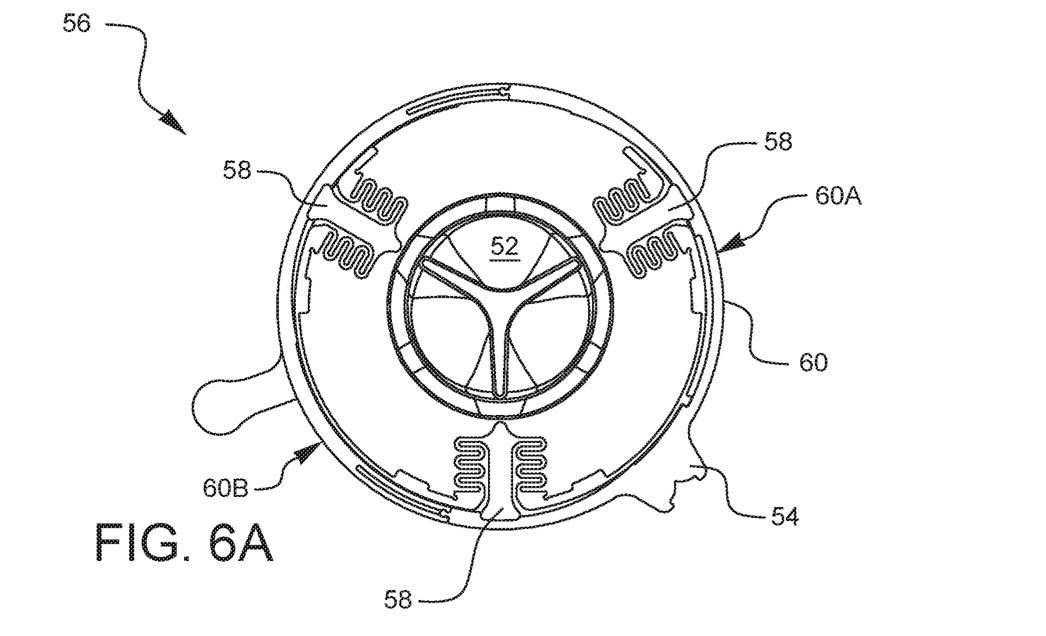
FIGS. 6A and 6B are top exposed views of the prosthetic suturing device illustrating one embodiment of a prosthetic retainer in a disengaged state and an engaged state, respectively, for retaining a prosthetic heart valve.
Figure 6B:
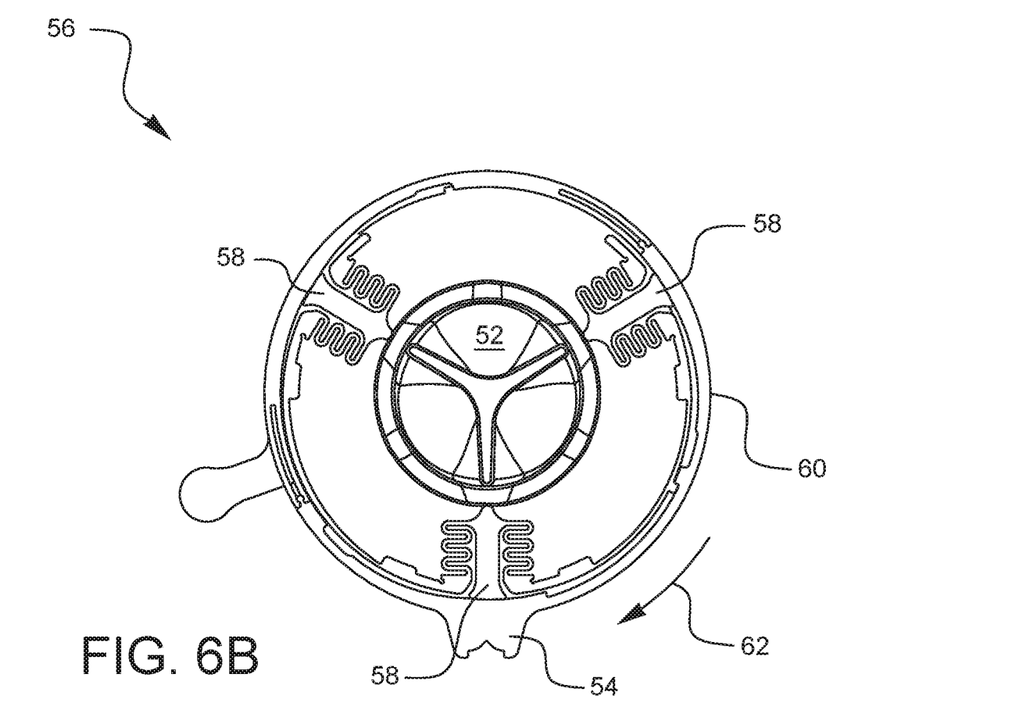

FIGS. 6A and 6B are top exposed views of the prosthetic suturing device illustrating one embodiment of a prosthetic retainer 56 in a disengaged state and an engaged state, respectively, for retaining the prosthetic heart valve 52. This embodiment of the prosthetic retainer 56 has a plurality of stud springs 58 which are slideably engaged with a stud spring ring 60. In this embodiment, the stud spring ring 60 is made from two substantially semicircular pieces 60A and 60B which couple together to make the stud spring ring 60. The inner surface of the stud spring ring 60 varies in how far it protrudes towards the stud springs 58. In the disengaged position of FIG. 6A, the stud spring ring 60 does not interfere with the stud springs 58 enough to push them into contact with the prosthetic valve 52. In the engaged position of FIG. 6B, however, the prosthetic retainer tab 54 has been rotated clockwise (from the point of view of FIG. 6B), thereby rotating the stud spring ring 60 such that sections of the interior of the stud spring ring 60, which interfere more with the stud springs 58, push the stud springs 58 into contact with a sewing cuff 64 of the prosthetic valve 52. Although not shown in this view, the device 30 has a prosthetic receiver which helps the prosthesis 52 to be positioned properly within the device 30. The prosthetic retainer 56 illustrated in FIGS. 6A and 6B is used to hold the prosthesis 52 within the device's prosthetic receiver for suturing as will be described further in this specification.

In a surgical context, a prosthesis such as the prosthetic valve 52 would be loaded into and retained within the prosthetic suturing device 30 as has been described above. The ferrule platen 46 which was removed from the device 30 prior to the loading of the prosthesis 52 is available to be loaded with sutures. As a non-limiting example, this specification will consider a cardiac surgical procedure to replace an aortic valve. The surgeon gains access to the aortic root via an aortotomy made in the ascending aorta. The leaflets of the diseased valve are dissected and removed. A series of sutures are then placed around the aortic annulus using a mattress suture stitch for each suture. The number of sutures placed around the annulus will vary based on a number of factors, including, but not limited to the size of the patient's annulus and/or surgeon preference. For the sake of discussion, this specification considers an example where twelve sutures are placed around the annulus. In a minimally invasive cardiac surgical procedure, the sutures may be placed through a very small incision between the patient's ribs using an automated suturing device such as the RAM® Device, available from LSI Solutions, Inc. of Victor, N.Y. (www.lsisolutions.com). The ends of each suture will have small metal cylinders on them called ferrules. With twelve separate sutures being placed, the 24 ends of those sutures need to be managed and kept organized to avoid suture tangling and to ensure that corresponding suture ends may be identified. To further complicate the situation, different surgeons may proceed in a different order depending on how they prefer to approach the surgery. The aortic valve has three commissure points which are located at one hundred twenty degree positions around the aortic annulus. Some surgeons prefer to place separate sutures at the commissure points first and then fill in sutures in the spaces between. Other surgeons prefer to start at one of the commissures and work their way counterclockwise or clockwise around the annulus in consecutive order.

Figure 7:
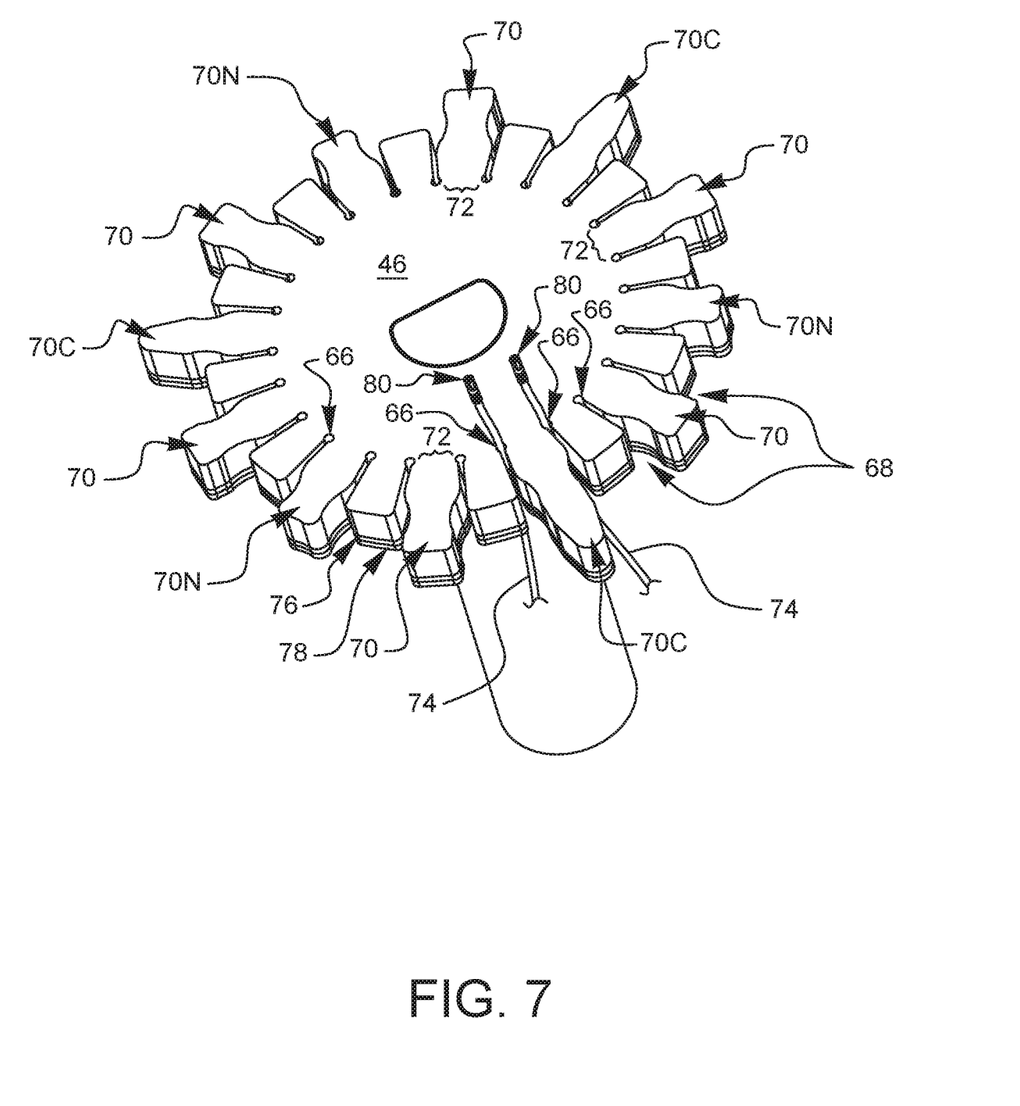
FIG. 7 illustrates two ferruled ends of a suture being loaded into a set of ferrule receivers in the ferrule platen of FIG. 3.

The ferrule platen 46, shown in FIG. 7, is designed to accommodate whichever way a surgeon prefers to work. The ferrule platen 46 has twenty-four ferrule holders 66 arranged in a circular pattern. In other embodiments, there could be a greater number or a lesser number of ferrule holders. Also, other embodiments might have the ferrule holders 66 arrayed in a different shape. The circular shape in the embodiment of FIG. 7 is compatible with the shape and dimensions of the sewing cuff for the prosthetic heart valve 52 which is being held in the prosthetic suturing device 30. Slots 68 extend from the periphery of the ferrule platen 46 to each ferrule holder 66. The slots 68 are wide enough to allow suture to be passed therethrough but not wide enough to allow a ferrule to pass. An indexing tab (either 70, 70N, or 70C) extends on the periphery of the ferrule platen 46, each indexing tab between a corresponding pair of ferrule holders 72. In this embodiment, there are three commissure indexing tabs 70C, one for each of the Left-Non Commissure (LN com), the Right-Non Commissure (RN com), and the Left-Right Commissure (LR com). Since we are working with an embodiment meant to be used with an aortic annulus which needs twelve sutures, there are twelve indexing tabs in this example. The commissure indexing tabs 70C are located one hundred twenty degrees apart. With twelve total sutures, three of those sutures will be for the commissures. This leaves nine sutures, and three of those nine sutures will be located in each of the three spaces between the commissures. The mid-point between the commissures may be referred to as the nadir, and the ferrule platen 46 has three nadir indexing tabs 70N. For the convenience of the surgical staff and for reference, the commissure indexing tabs 70C are labelled in this embodiment ("LN com", "RN com", and "LR com") and they also have a distinct shape which protrudes farther than the other indexing tabs. The nadir indexing tabs 70N are also labelled "ndr" in this embodiment.

The ends of a suture 74 are being loaded into the ferrule platen 46 in FIG. 7. Specifically, the ends of the suture 74 are being loaded into the ferrule holders 66 which correspond to the Left-Non Commissure as denoted by the commissure indexing tab 70C which is labelled "LN com". In this embodiment, the ferrule platen 46 has two lower layers: a ferrule stop plate 76 and a suture retaining plate 78. The ferrule stop plate 76 has holes and slots which correspond to the ferrule platen 46, but the holes are sized to prevent a ferrule placed into the ferrule platen 46 from passing through the ferrule stop plate 76. The suture retaining plate 78 may be configured to have even tighter holes and slots in order to grasp a suture placed therein in order to help keep the ferrules placed into the ferrule platen 46 from falling out. Some embodiments may not have a suture retaining plate. Other embodiments may incorporate the features of the ferrule stop plate 76 and/or the suture retaining plate 78 into the ferrule platen 46.

The ends of suture 74 in FIG. 7 have ferrules 80 on them. As shown in FIG. 7, the ferrules 80 still need to be pulled down into the ferrule holders 66. When fully installed, the ferrules 80 will be held within the ferrule holders 66. As the cardiac surgical procedure continues, all of the twenty-four suture ends for the twelve annular sutures can be placed within appropriate slots/ferrule holders of the ferrule platen 46 in order to keep them organized.

Figure 8:
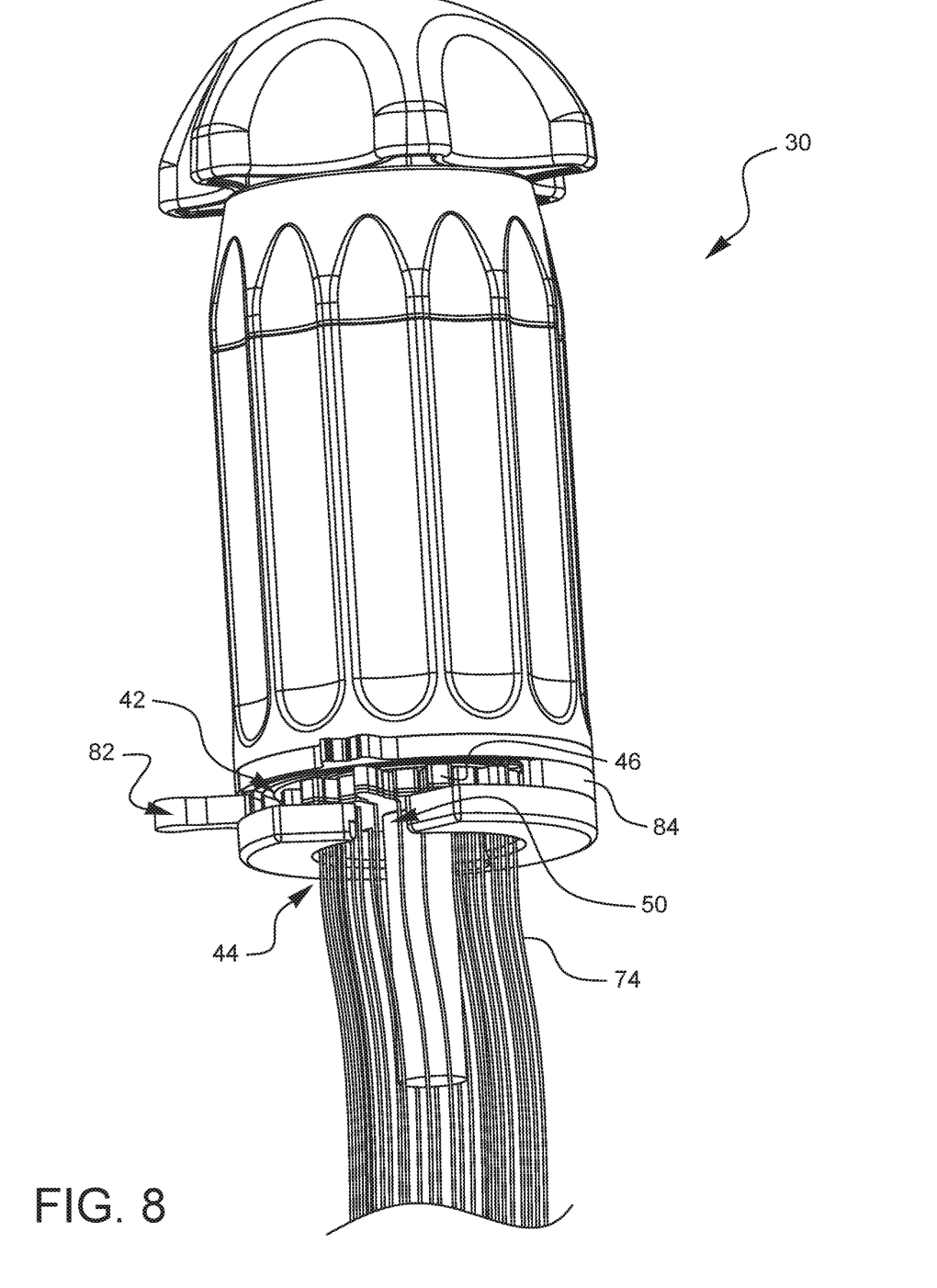
FIG. 8 illustrates a fully loaded ferrule platen loaded into the prosthetic suturing device.
Figure 9:
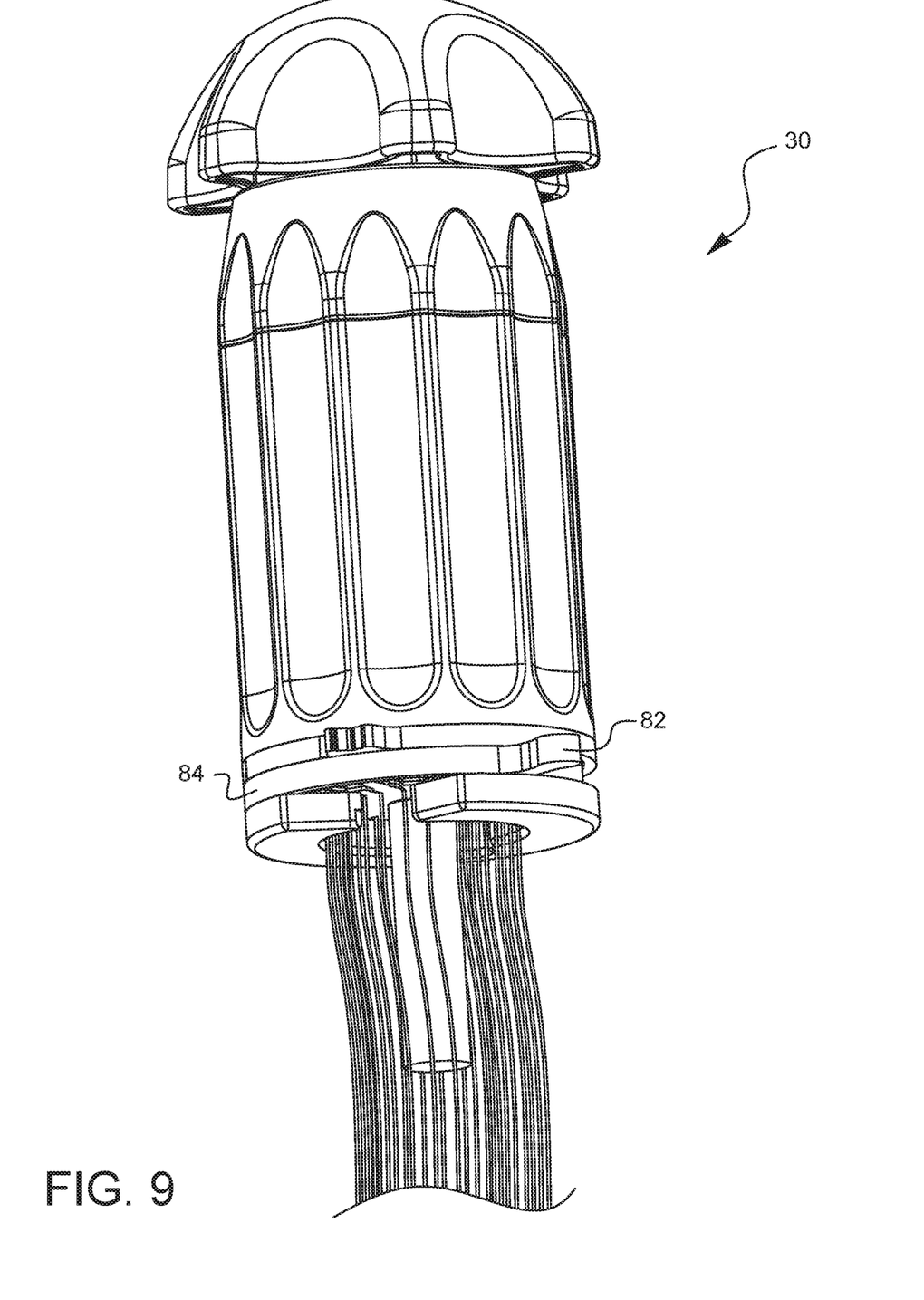
FIG. 9 illustrates a platen locking ring engaged to hold the ferrule platen in place within the prosthetic suturing device.

As shown in FIG. 8, a fully loaded ferrule platen 46 can be placed back into the platen opening 42 of the prosthetic suturing device 30. The sutures 74 can pass through the stem notch 50 so that they hang through the prosthetic opening 44. As illustrated in FIG. 9, a platen locking tab 82 on a platen locking ring 84 may be used to rotate the platen locking ring 84 into a position which holds the ferrule platen in a desired location within the prosthetic suture device 30.

Figure 10:
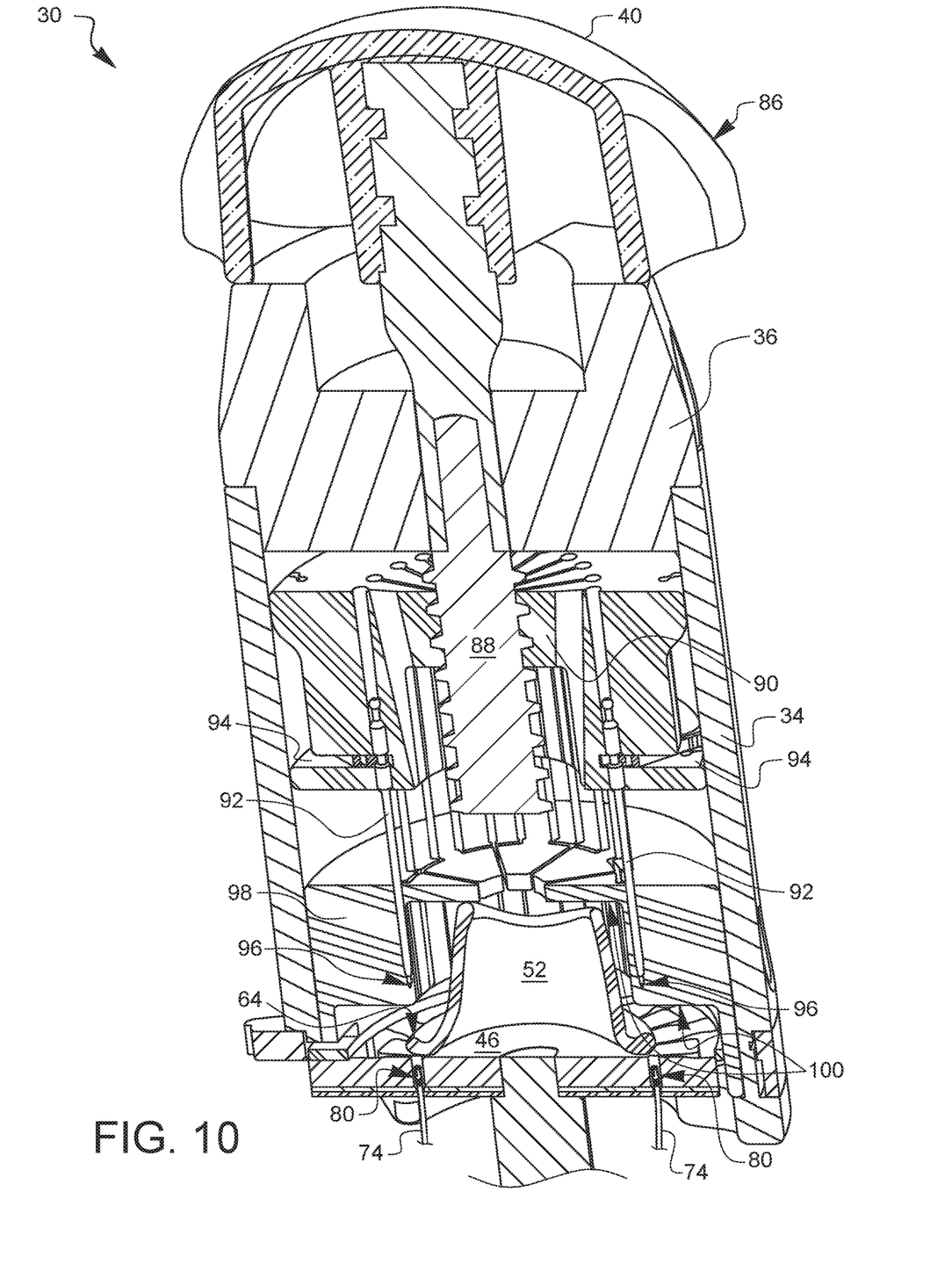
FIG. 10 is a perspective cross-sectional view of the prosthetic suturing device.

FIG. 10 is a perspective cross-sectional view of the prosthetic suturing device 30 shown while loaded with a prosthetic aortic valve 52. For simplicity, only two ferrules 80 are shown in the ferrule platen 46. It should be understood, however, that each of the twenty four ferrules which may be loaded in the ferrule platen 46 would be manipulated the same way as will be discussed for the example ferrules 80.

In this embodiment, the actuator 40 has a control knob 86 which is coupled to a drive screw 88. The drive screw 88 is in threaded engagement with a needle press 90 which is slideable within the main housing 34. The control knob 86 is free to rotate with respect to the top housing 36, but is constrained from moving axially with respect to the top housing 36. Thus, rotation of the control knob 86 in one direction will cause the needle press 90 to move towards the ferrule platen 46, while rotation of the control knob 86 in the opposite direction will cause the needle press 90 to move away from the ferrule platen 46 as the threads of the drive screw 88 engage the corresponding threads in the needle press 90. A plurality of needles 92 (one for each ferrule holder 66 in the ferrule platen 46) are coupled to the needle press 90. Each of the needles 92 is held by the needle press 90 in alignment with a corresponding ferrule holder 66 of the ferrule platen 46. In this embodiment, one or more needle latches 94 hold the needles 92 in place within the needle press 90.

As shown in FIG. 10, the needles 92 are in a retracted position. The tip 96 of each needle 92 is housed within a needle track 98. The needle track 98 is fixed with respect to the main housing 34 in this embodiment. Since the needle tips 96 are within the needle track 98 in this retracted position, the users are protected from being pierced or cut by the needles when loading the prosthetic valve 52 into the device. The needle track 98 may also define a prosthetic receiver 100 which can provide clearance for fragile structures of the prosthesis (such as prosthetic valve leaflets) and may also provide a surface for less fragile structures (such as a prosthetic sewing cuff) to rest against for support and orientation purposes before the prosthetic retainer is engaged to hold the prosthesis 52 in place.

Once the prosthesis 52 has been retained in place and the loaded ferrule platen 46 has been locked into place, as illustrated in FIG. 10, the control knob 86 may be rotated to cause the needle press 90 to advance the needle tips 96 out of the needle track 98 towards and through the sewing cuff 64 of the prosthetic valve 52 and into contact with corresponding ferrules 80. The needle tips 96 are sized to have an interference fit with the openings of the ferrules 80, thereby coupling the ferrules 80 to the needle tips 96. The control knob 86 may then be rotated in the opposite direction to draw the needles 92 back towards their starting position. Since the ferrules 80 are coupled to the needle tips 96, this will pull the ends of the suture 74 through the prosthetic sewing cuff 64. After the needles 92 have been retracted, the platen locking ring 84 may be rotated back to the open position of FIG. 8 by the platen locking tab 82 so that the ferrule platen 46 may be removed from the device 30. Similarly, the prosthetic retaining tab 54 may be rotated to release the prosthetic valve 52 (prosthetic retaining features discussed previously are not shown in FIG. 10 for simplicity). The prosthesis 52 may be removed, and the user will find that all of the sutures have been passed through the sewing cuff 64 in a single action. In addition to the suture organization benefits, this device has the potential to greatly reduce the amount of time it takes to suture and install a prosthesis. Such time savings can be highly beneficial to the patient, especially in a cardiac surgical procedure where the patient is often on cardio-pulmonary bypass (CPB). Shorter time on CPB has been shown to reduce morbidity and mortality in surgical patients.

Although the actuator illustrated in the embodiments above utilizes a drive screw to advance the needles through the prosthetic sewing cuff, other embodiments may utilize other types of actuators, including, but not limited to lever actuators, gear-based actuators, motorized actuators, solenoid driven actuators, or any combination and/or plurality thereof.

While the embodiments discussed above were configured to be used with a prosthetic cardiac valve, other embodiments may be configured to be used with other types of prosthetic devices, such as, but not limited to, an annuloplasty ring or a sewing cuff for a ventricular assist device such as the HeartMate III™ device.

Various advantages of a prosthetic suturing device and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A prosthetic suturing device, comprising:
a housing;
a needle press slideably engaged with the housing;
a plurality of needles coupled to the needle press;
a prosthetic retainer;

a ferrule platen having a plurality of ferrule holders, each corresponding to one of the plurality of needles; and an actuator configured to move the needle press from a retracted position where needle tips of the plurality of needles are away from the ferrule platen to an engaged position where the needle tips of the plurality of needles are at least partially within the ferrule holders of the ferrule platen.

2. The prosthetic suturing device of claim 1, wherein the plurality of needles are coupled to the needle press by one or more needle latches.

3. The prosthetic suturing device of claim 1, wherein the plurality of needles are arranged on the needle press in a substantially circular pattern.

4. The prosthetic suturing device of claim 1, wherein the prosthetic retainer comprises:

one or more stud springs;

a stud spring ring engageable with the one or more stud springs; and a prosthetic retainer tab coupled to the stud spring ring.

5. The prosthetic suturing device of claim 1, wherein the ferrule platen further comprises a ferrule stop plate.

6. The prosthetic suturing device of claim 1, wherein the ferrule platen further comprises a suture retaining plate.

7. The prosthetic suturing device of claim 1, wherein the ferrule platen further comprises a plurality of indexing tabs.

8. The prosthetic suturing device of claim 7, wherein the plurality of indexing tabs comprise one or more commissure indexing tabs.

9. The prosthetic suturing device of claim 7, wherein the plurality of indexing tabs comprise one or more nadir indexing tabs.

10. The prosthetic suturing device of claim 1, further comprising a platen stem coupled to the ferrule platen.

11. The prosthetic suturing device of claim 1, wherein the housing defines a platen opening.

12. The prosthetic suturing device of claim 1, wherein the housing defines a prosthetic opening.

13. The prosthetic suturing device of claim 1, wherein the housing defines:

a platen opening;

a prosthetic opening; and a stem notch which joins the platen opening and the prosthetic opening.

14. The prosthetic suturing device of claim 1, further comprising a needle track coupled to the housing.

15. The prosthetic suturing device of claim 14, wherein the needle track comprises a plurality of holes, each corresponding to a different one of the plurality of needles.

16. The prosthetic suturing device of claim 14, wherein the needle tips are located within the needle track while the device is in the retracted position.

17. The prosthetic suturing device of claim 14, wherein the needle track further defines a prosthetic receiver.

18. The prosthetic suturing device of claim 1, further comprising a prosthetic receiver.

19. The prosthetic suturing device of claim 1, wherein the actuator comprises:

a control knob; and a drive screw coupled to the control knob.

20. The prosthetic suturing device of claim 19, wherein the drive screw is in threaded engagement with the needle press.

21. The prosthetic suturing device of claim 1, wherein the actuator comprises a device selected from the group consisting of a lever, a gear, a motor, and a solenoid.

22. The prosthetic suturing device of claim 1, wherein the prosthetic retainer is configured to hold a prosthetic device selected from the group consisting of a prosthetic aortic valve, a prosthetic mitral valve, a prosthetic heart valve, a sewing cuff for a ventricular assist device, and an annuloplasty ring.

23. A method of prosthetic suturing, comprising:

retaining a prosthesis in a prosthetic receiver of a prosthetic suturing device;

loading a plurality of ferrules, each ferrule coupled to a different suture end, into a ferrule platen;

locking the loaded ferrule platen into the prosthetic suturing device;

actuating a plurality of needles substantially simultaneously through the retained prosthesis and into coupling contact with the plurality of ferrules loaded into the ferrule platen; and retracting the plurality of needles substantially simultaneously back through the retained prosthesis to pull the different suture ends through the prosthesis.

* * * * *